United States Patent
Giesecke (10) Patent No.: US 8,759,793 B2
(45) Date of Patent: Jun. 24, 2014

(54) METHOD FOR DETERMINING MATERIAL PARAMETERS OF A DOPED SEMICONDUCTOR SUBSTRATE BY MEASURING PHOTOLUMINESCENT RADIATION

(75) Inventor: Johannes Giesecke, Freiburg (DE)

(73) Assignee: Fraunhofer-Gesellschaft zur Förderung der Angewandten Forschung E.V., München (DE)

( * ) Notice: Subject to any disclaimer, the term of this patent is extended or adjusted under 35 U.S.C. 154(b) by 0 days.

(21) Appl. No.: 13/695,452

(22) PCT Filed: Apr. 13, 2011

(86) PCT No.: PCT/EP2011/001848
§ 371 (c)(1),
(2), (4) Date: Jan. 3, 2013

(87) PCT Pub. No.: WO2011/134602
PCT Pub. Date: Nov. 3, 2011

(65) Prior Publication Data
US 2013/0146787 A1    Jun. 13, 2013

(30) Foreign Application Priority Data
Apr. 30, 2010  (DE) .................... 10 2010 019 132

(51) Int. Cl.
*G01N 21/64*    (2006.01)
(52) U.S. Cl.
USPC ...................................................... 250/459.1
(58) Field of Classification Search
USPC ...................................................... 250/459.1
See application file for complete search history.

(56) References Cited

U.S. PATENT DOCUMENTS

2003/0094579 A1    5/2003  Hasegawa et al.

FOREIGN PATENT DOCUMENTS

| DE | 102008013068 | 6/2012 |
|---|---|---|
| EP | 0545523 | 6/1993 |
| EP | 0563863 | 10/1993 |
| WO | 2005017996 | 2/2005 |
| WO | 2008014537 | 2/2008 |
| WO | 2008037002 | 4/2008 |
| WO | 2008052237 | 5/2008 |

OTHER PUBLICATIONS

Chouffot et al., "Modulated photoluminescence as an effective lifetime measurement method: Application to a-Si:H/c-Si heterojunction solar cells," 2009, Materials Science and Engineering B vol. 159-160, pp. 186-189.*

(Continued)

*Primary Examiner* — Kiho Kim
(74) *Attorney, Agent, or Firm* — Volpe and Koenig, P.C.

(57) ABSTRACT

Method for determining material parameters of a doped semiconductor substrate, including: applying electromagnetic excitation radiation in order to produce luminescent radiation in the semiconductor substrate, the temporal profile of the excitation radiation intensity is periodically modulated, so that the rate of generation of charge carrier pairs in the substrate has a maximum and minimum during an excitation period, and at least the relative temporal profile of the rate of generation G(t) is determined by time-dependent measurement of the excitation radiation intensity, time-resolved measuring luminescent radiation intensity emanating from a measuring region, at least the relative temporal profile of the intensity of the luminescent radiation $\Phi(t)$ is measured during an excitation period, determining a material parameter of the semiconductor substrate based on G(t) and $\Phi(t)$. The effective lifetime of the substrate is determined from the time difference between the maximum of $G(t)$ and a corresponding maximum of $\Phi(t)$.

10 Claims, 3 Drawing Sheets

(56) References Cited

OTHER PUBLICATIONS

Eli Yablonovitch, "Inhibited spontaneous emission in solid-state physics and electronics," May 18, 1987, Physical Review Letters, vol. 58, No. 20, pp. 2059-2062.*

Nuban et al., "Room temperature scanning photoluminescence for mapping the lifetime and the doping density in epitaxial layers," 1997, Materials Science and Engineering, vol. B44, pp. 125-129.*

Wurfel, P. et al., "Diffusions Lengths of Silicon Solar Cells from Luminescence Images", Journal of Applied Physics, 101; 123110, (2007). Published Jun. 27, 2007.

Trupke, T., et al., "Photoluminescence Imaging of Silicon Wafers", Applied Physics Letters, 89: 044107, (2006). Published Jul. 26, 2006.

Trupke, T., et al., "Self-Consistent Calibration of Photoluminescence and Photoconductance Lifetime Measurements", Applied Physics Letters, 87: 184102, (2005). Published Oct. 24, 2005.

Sinton, R., et al., "Quasi-Steady-State Photoconductance, A New Method for Solar Cell Material and Device Characterization", 25th IEEE PVSC, Washington, D.C., (1996).

Cuevas, A., "The Paradox of Compensated Silicon", Commad IUMRSICEM08, Sydney, (2008).

Trupke, T., et al., "Effective Excess Carrier Lifetimes Exceeding 100 Milliseconds in Float Zone Silicon Determined from Photoluminescence", In: Proceedings of the 19th EC PVSEC, Paris, France, 2001, pp. 758-761.

Brasil, M., et al., "Carrier Dynamics Investigated by Time-Resolved Optical Spectroscopy", In: Phys. Stat. Sol., vol. 190, No. 3, 2002, pp. 647-650.

Piao, Z.S., et al., "Intensity Variation of Photoluminescence in InxGa1-xAs/GaAs Multi-Quantum-Well Structures", In: Appl. Phys. Lett., vol. 65, No. 3, Jul. 1994, pp. 333-335.

Bruggemann, R. et al., "Modulated Photoluminescence Studies for Lifetime Determination in Amorphous-Silicon Passivated Crystalline-Silicon Wafers", Journal of Non-Crystalline Solids 352 (2006), pp. 1888-1891.

Altermatt, P.P., et al., "Injection Dependence of Spontaneous Radiative Recombination in Crystalline Silicon: Experimental Verification of Theroretical Analysis", Appl. Phys. Lett., vol. 88, (2006).

\* cited by examiner

METHOD FOR DETERMINING MATERIAL PARAMETERS OF A DOPED SEMICONDUCTOR SUBSTRATE BY MEASURING PHOTOLUMINESCENT RADIATION

BACKGROUND

The invention relates to a method for determining material parameters of a doped semiconductor substrate by measuring photoluminscent radiation.

In doped semiconductor substrates, particular in silicon wafers, it is known to obtain conclusions about the material parameters of the semiconductor substrate based on a luminescent radiation generated in said semiconductor structure and its measurement. In particular the measurements of the luminescent radiation are used to gather information about the material quality with regards to the effective life time of the minority charge carriers or the effective duration of diffusion corresponding thereto.

Here, it is known to determine the diffusion length/life time of the semiconductor material from the measurement of the luminescent radiation. Respective methods are described in literature, for example in Würfel, P. et al., "Diffusions Lengths of Silicon Solar Cells from Luminescence Images", Journal of Applied Physics, 101; 123110, 2007, or in Trupke, T. et al, "Photoluminscence Imaging of Silicon Wafers", Applied Physics Letters, 89: 044107, 2006.

Furthermore, measuring methods are known in which the impinging of the semiconductor substrate occurs with modulated excitation radiation so that the rate of generation G of charge carrier pairs in the semiconductor substrate, generated by the excitation radiation, is temporarily inhomogeneous and shows at least one maximum. Typically a periodic, sinusoidal modulation is used. Here the modulation occurs such that a quasi static condition is achieved. The respective measuring method with an assessment of the photoluminescent radiation is known as the quasi steady-state photoluminescence life time measurements (QSS-PL) and described for example in T. Trupke and R. A. Bardos, $31^{st}$ IEEE PVSC, Orlando, 2005.

In the quasi steady-state photoluminescence life time measurement methods the quantitative determination of the excess charge carrier density $\Delta n$ is essential to determine for example the effective life time $\tau$ of the minority charge carriers. For calibration of the quasi steady-state photoluminescence measuring methods it is known to determine respective calibration parameters via the self-consistency method, such as described in T. Trupke, R. A. Bardos, M. D. Abbott, "Self-Consistent Calibration of Photoluminescence and Photoconductance Lifetime Measurements", Applied Physics Letters, 87: 184102, 2005.

In this self-consistent calibration the knowledge of the concentration of electrically active doping atoms N in the semiconductor substrate (in the following called doping concentration for reasons of simplification) is necessary as well as the time-dependent generation rate G(t) during the impingement of the semiconductor substrate with respectively modulated excitation radiation, here quantitatively. Here, particularly the determination of the doping concentration N with conventional methods is problematic (such as an eddy-based measuring method, cf. Sinton. R. et al, "Quasi Steady-State Photoconductance, a new method for solar cell material and device characterization", $25^{th}$ IEEE PVSC, Washington D.C., 1996). Presently the knowledge becomes generally accepted in professional literature that in many novel materials for the solar cell production, such as in multi-crystalline silicon, conventional methods for the determination of the doping concentration N reach their limits, because they require the precise quantitative assumptions regarding the mobility of the charge carriers, which cannot be obtained here (cf. Cuevas, A. "The paradox of compensated silicon", COMMAD IUMRSICEM08, Sydney, 2008).

SUMMARY

The invention described here is therefore based on the objective of providing a method for measuring minority charge carrier life times based on photoluminescence, independent from the previous assumption via charge carrier mobility, particularly a method independent from the determination of the doping concentration N generally additionally necessary for the lift time measurements based on photoluminescence.

This objective is attained in a measuring method according to the invention. Advantageous embodiments of the measuring methods are disclosed below and in the claims.

In the processing step A the doped semiconductor substrate is impinged with electromagnetic excitation radiation in order to generate luminescent radiation in the semiconductor substrate, with the temporal progression of the intensity of the excitation radiation being modulated. The periodic modulation occurs such that the rate of generation G of charge carrier pairs in the semiconductor substrate shows a maximum and a minimum due to the excitation radiation during the excitation period. Furthermore, the temporal progression of the rate of generation G(t) is determined via a time-dependent measurement of the intensity of the excitation radiation.

In the processing step B a time-resolved measurement occurs of at least the relative intensity of the luminescent radiation emitted by a measuring area of the semiconductor substrate, with the temporal progression of the intensity of the luminescent radiation $\Phi(t)$ being measured at least during the excitation period of the excitation radiation.

In a processing step C at least one material parameter of the semiconductor substrate is determined depending on the temporal progression G(t) of the rate of generation and the temporal progression of the intensity of the luminescent radiation $\Phi(t)$.

It is essential that in step C the effective life time t of the minority charge carrier of the semiconductor substrate is determined at least at the excess charge carrier density $\Delta n_{max}$ maximally achieved during an excitation period, in which the temporal difference between the maximum of G(t) and a corresponding maximum $\Phi(t)$ being determined.

The invention in based on the acknowledgement of the applicant that in the particular case of injection-independent life time the effective life time of the semiconductor substrate can surprisingly be determined in a particularly easy fashion if the above-mentioned condition of a quasi steady-state measuring method is fulfilled:

The modulation of the excitation radiation leads to a respective modulation of the generation rate G(t) of charge carrier pairs in the semiconductor substrate. The time-dependently measured luminescent radiation $\Phi(t)$ also shows at least one maximum with regards to intensity. The maximum of intensity of the luminescent radiation is given however temporarily off-set slightly later in reference to the maximum of the rate of generation G(t). In the method according to the invention this temporal off-setting is determined. In the particular case of the injection-independent life time this off-setting is equivalent to the effective life time in the semiconductor substrate.

Preferably, in step A the periodic modulation occurs such that the maximum of the rate of generation G amounts to less than 50%, preferably less than 20%, particularly less than 10% of the maximum of the rate of generation. This way, high precision is ensured for determining the life time.

Preferably, in step A the modulation of the rate of generation occurs sinusoidal, because here a comparatively simple mathematic treatment results.

Preferably, in the periodic modulation the period term T is selected greater than the expected life time, particularly at least by a factor of 30, further at least by a factor of 50, preferably greater by at least a factor of 100. This way the presence of quasi steady-state measuring conditions is ensured.

It is known that the effective life time is generally dependent on the excess charge carrier density $\Delta n$ given in the semiconductor substrate. By this dependency the temporal off-set between the maxima of the rate of generation and the intensity of the photoluminescence is also influenced, so that it cannot any longer be identified with the life time and/or lead to an error in the determination.

However, in the following preferred embodiment, by expanding the processing steps A, B, and C of the method, the precise determination of the life time can be performed based on the measurement of the temporary off-set between the maxima of the rate of generation and the intensity of photoluminscent radiation. For this purpose, preferably an iteration method shall be performed in order to determine the life time $\tau_0 = \tau(\Delta n_{max})$ allocated to the excess charge carrier density maximally achieved during the excitation period.

For this purpose, the processing steps A and B shall be advantageously expanded such that the impinging with excitation radiation, the measurement of the rate of generation, as well as the measurement of the intensity of the photoluminescent radiation shall occur at least for two slightly different maximum excitation intensities. Preferably they differ relatively at a range from 5% to 25%, preferably at a range from 10-% to 20%, further preferred by approximately 15%.

Accordingly, the processing steps A and B are therefore performed at least twice, with the first and the second execution being different with regards to the maximum intensities of excitation.

In the processing step C the calculated temporal off-sets of the respective maxima of the rate of generation and the intensity of photoluminescence are used at different conditions of excitation. The determination of the material parameters occurs here preferably via an iteration method.

The determination of the life time allocated to the excess charge carrier density maximally achieved during an excitation period occurs preferably via the above-mentioned iteration method and is preferably dependent on at least two temporal off-sets determined under different excitation conditions between the respective maximum of the rate of generation and the intensity of the excitation radiation.

The iteration method mentioned is used to find the injection-dependent life time $\tau(\Delta n)$, which, inserted into the differential equation (see equation 4) describing the charge carrier dynamic, correctly reflects the temporal differences measured of the maxima of G(t) and $\Phi(t)$.

The iteration method for the determination of the life time is preferably embodied as follows:

The temporal off-sets between the maxima of the rate of generation and the intensity of the photoluminescent radiation measured for both measurements with respectively slightly different excitation intervals shall here be marked $\Delta t_{0,i}$, the allocated maximum rate of generation with $G_{0,i}$. In the following the index j indicates the respective iteration step, the index f indicates the various excitation intensities. In one initial step (j=1) it is assumed that the temporal off-sets $\Delta t_{0,i}$ measured were equivalent to the life times $\tau_{1,i} = \Delta t_{0,i}$. The allocated excess charge carrier densities would then be $\Delta_{n1,i} = \tau_{1,i} G_{0,1}$. The $\tau_{1,j}(\Delta n_{1,i})$ are then inserted for an approximation, preferably a linear approximation, of the injection-dependent life time $\tau(\Delta n)$ in the differential equation (equation 4) describing the charge carrier dynamic in turn in order to calculate from its numeric solution the time off-sets $\Delta_{fl,i}$. A correction of the life time is then determined as follows:

$$\tau_{j+1,i} = \tau_{j,i} + \epsilon(\Delta t_{0,i} - \Delta t_{j,i}) \quad (1)$$

This method is now repeated until the life time converges, i.e. the change of the life time from one iteration step to the next one is negligible. Here, the number $0 < \epsilon < 1$ is selected so small that convergence is possible. Typically 10-20 iteration steps are sufficient in order to achieve convergent life times.

For the determination of the effective life time using the method according to the invention no knowledge of the doping concentration N of the semiconductor substrate is necessary.

Using the method according to the invention therefore allows the determination of an effective life time $\tau$ of the semiconductor substrate in the range of the excess charge carrier density $\Delta n_{max}$.

As already mentioned, similar to the QSS-PL—methods of prior art in the method according to the invention a quasi steady-state measurement occurs as well. This means that the period term of the modulation of the excitation radiation is long in reference to the effective life time of the minority charge carrier of the semiconductor substrate.

In a preferred embodiment of the method according to the invention in step C the determination of the effective life time $\tau(\Delta n)$ of the semiconductor substrate occurs depending on the excess charge carrier density $\Delta n$ and/or the determination of the doping concentration N of the semiconductor substrate. The determination occurs dependent on the at least qualitatively measured temporal progression $\Phi(t)$ of the intensity of the photoluminescence radiation, the quantitatively determined temporal progression of the rate of generation G(t) and the life time $\tau_0 = \tau(\Delta n_{max})$ according to the above-described processing steps.

In this preferred embodiment of the method according to the invention the determination is based on the acknowledgement that when knowing the quantitative temporal progression of the rate of generation G(t) it is possible to determine the effective life time $\tau$ depending on the excess charge carrier density $\Delta n$, i.e. not only for the immediate range about the excess charge carrier density $\Delta n_{max}$, and further the doping concentration N of the semiconductor substrate. Thus, in this preferred embodiment no previous knowledge of the doping concentration N of the semiconductor substrate is necessary. Furthermore it is here possible to determine the doping concentration from the measurements themselves.

In the embodiment of the method according to the invention for determining the doping concentration N preferably in step A the periodic modulation occurs such that the minimum of the rate of generation G amounts to less than 15%, preferably less than 10%, particularly less than 5% of the maximum rate of generation. This way, high precision is ensured for the determination of the doping concentration N.

The knowledge of the qualitative temporal progression of the intensity of the photoluminescent radiation $\Phi(t)$ and the quantitative temporal progression of the rate of generation G(t) in addition to the knowledge of the life time $\tau_0 = \tau(\Delta n_{max})$ from the above-described process is sufficient to determine both the injection-dependent life time $\tau(\Delta n)$ as well as the doping concentration N. From the curvature of the temporal progression of the intensity of the photoluminescent radiation $\Phi(t)$, (e.g., in case of sinusoidal excitation) when knowing the qualitative rate of generation at the maximum $G_0$, the doping concentration of the semiconductor substrate can be determined depending on the curvature of the temporal progression of the relative (normed to a maximum of 1) intensity of the photoluminescent radiation $\Phi(t)$ at the corresponding maximum at the point of time $t=t_{max}$. This occurs preferably as follows:

$$\frac{\partial^2 \Phi'(t)}{\partial t^2}\bigg|_{t=t_{max}} = -2\frac{\pi^2}{T^2}\frac{2G_0\tau_0 + N}{G_0\tau_0 + N} \qquad (2)$$

Due to the fact that all parameters occurring in this equation are known, except for the doping concentration N, from the measurement of G(t) and $\Phi(t)$ and additionally the term $2\pi^2/T^2$ of the curvature which is equivalent to a rate of generation standardized to a maximum of 1 at its maximum, the equation can be resolved for N and thus N can be determined.

Here, preferably in step C the description of the temporal progression of the rate of generation G(t) occurs via a mathematic model, which shows a first set of at least two fit parameters and the description of a temporal progression of the intensity of the photoluminescent radiation $\Phi(t)$ via a mathematic model analog to the first one, which second set comprises at least two fit parameters. The determination of the fit parameters of the first set occurs depending on the time-dependently measured intensity of the excitation radiation and accordingly the determination of the fit parameters of the second set occurs depending on the time-dependently measured intensity of the photoluminescent radiation.

Accordingly, in this preferred embodiment a mathematical description is given based on the determined fit parameters of the time-dependent rate of generation in the semiconductor substrate in a quantitative form and the time-dependent photoluminescent radiation in a qualitative form. The determination of the effective life time $\tau$ of the semiconductor substrate depending on the excess charge carrier density $\Delta n$ and/or the determination of the doping concentration N of the semiconductor substrate occurs depending on the first and the second set of fit parameters.

Preferably, here the modulation of the excitation radiation occurs sinusoidal and the mathematical model for the temporal progression of the rate of generation and for the temporal progression of the intensity of the photoluminescent radiation preferably shows a sinusoidal function and a frequency and a phase location respectively in the form of fit parameters.

The use of sinusoidal modulation for the excitation radiation is already known from the methods of the QSS-PL measurement of prior art. This modulation of the excitation radiation leads to a mathematically simple model for the temporal progression of the intensity of the photoluminescent radiation and the rate of generation so that in a simple fashion and with easy mathematic fit-methods of prior art a determination of the above-mentioned fit-parameters is possible.

Here, preferably the description of the rate of generation occurs by the equation 2 with the maximum rate of generation $G_0$, the period term of the sinusoidal modulation T, and the point of time of the maximum generation to:

$$G(t) = G_0\cos^2\left(\frac{\pi}{T}(t-t_0)\right) \qquad (3)$$

In the particular case of quasi steady-state excitation conditions ($\tau \ll T$) the excess charge carrier density results in the semiconductor substrate as a function of time as the solution of the time-dependent continuity equation $$\frac{\partial \Delta n(t)}{\partial t} + \frac{\Delta n(t)}{\tau(\Delta n(t))} = G(t) \qquad (4)$$

(with the injection dependency of the life time initially being negligible) as follows:

$$\Delta n(t) = G_0 \tau \cos^2\left(\frac{\pi}{T}(t-t_0-\tau)\right). \qquad (5)$$

i.e. the excess charge carrier density $\Delta n$ is equivalent to the rate of generation temporarily retarded by the life time and multiplied with the life time. With the initially unknown factor A and the doping concentration N the luminescent signal $\Phi(t)$ of the semiconductor substrate can be described as follows:

$$\Phi(t) = A \cdot \Delta n(t) \cdot (\Delta n(t) + N). \qquad (6)$$

With the phase $\alpha = n(t-t_0-\tau_0)/T$ and the doping concentration N then the description occurs of the time-dependent relative photoluminescent signal (standardized to a maximum of 1) via $$\Phi'(t) = \frac{G_0 \tau \cos^4\alpha + N\cos^2\alpha}{G_0\tau + N}. \qquad (7)$$

By a dual time deduction (cf. equation 2) an expression for the curvature of the relative luminescent intensity can be determined therefrom at its maximum, which includes the doping concentration. Due to the fact that $G_0$, $\tau_0$, and T are already known by the above-described fit-methods and procedures N remains the only unknown factor in the equation 2 and can be determined unambiguously.

Additionally and/or alternatively the effective life time $\tau_{eff}$ can be calculated, depending on the excess charge carrier density $\Delta n$, as follows: Using the known doping concentration N and the known life time at the maximum excess charge carrier density $\tau_0$ as well as the known maximum rate of generation $G_0$ the maximum excess charge carrier density $\Delta n_{max} = G_0\tau_0$ is also known. Furthermore, in the equation 6 the initially unknown factor A can be determined, which allows a determination of $\Delta n(t)$ by the resolution of the equation 6. The time-dependent excess charge carrier density can in turn be inserted into the continuity equation (equation 4) and then this (equation) can be resolved for the life time (since G(t) is known). This way, the life time can be determined as a function of the excess charge carrier density.

In particular for the determination of the doping concentration N of the semiconductor substrate it is advantageous if the maximum excess charge carrier density $\Delta n_{max} = G_0\tau_0$ is approximately equivalent to the basic doping concentration. Preferably the modulation of the excitation radiation is therefore selected such, conditional to the range of the life time and the doping concentration being known approximately, that the excess charge carrier density at maximum generation is approximately equivalent to the doping concentration to be expected.

Given that in most circumstances a significant dependency of the minority charge carrier—life time exists from the excess charge carrier density, based on the acknowledgement of the applicant it is necessary to consider this dependency also for the calculation of the doping concentration N according to the equation 2. From the above-described processing steps A, B, and C it is discernible that by measuring the rate of generation as well as the intensity of the photoluminescent radiation at two excitation intensities, preferably different by approx. 10%, both the life time $\tau_0$ as well as its incline $\gamma$ can be determined in the immediate proximity around the excess charge carrier density $\Delta n_{max}$:

$$\tau \approx \tau_0 + \gamma(\Delta n - \tau_0 G_0) \quad (8)$$

It can be shown that in consideration of the injection dependency this way the curvature of the photoluminescent intensity at its maximum (at the time $t=t_{max}$) relates to the life time as $$\left.\frac{\partial^2 \Phi'(t)}{\partial t^2}\right|_{t=t_{max}} = -2\frac{\pi^2}{T^2}\frac{2G_0\tau_0 + N}{G_0\tau_0 + N}\frac{1}{1-\gamma G_0}. \quad (9)$$

It has shown that this correction is necessary in most cases, because typically the parameter $\gamma$ is largely influential on the curvature of the photoluminescent intensity at its maximum.

In another preferred embodiment of the method according to the invention the quantitative determination of the doping concentration N and/or the effective life time of the minority charge carrier $\tau(\Delta n)$ occurs depending on the excess charge carrier density $\Delta n$ by performing the processing steps A and B, namely at two very different measuring conditions:

A first measuring condition is selected such that low injection conditions are given in the semiconductor substrate and a second measuring condition is selected such that high injection conditions are given.

Low injection conditions mean that the product of the maximum rage of generation $G_0$ and the effective life time of the minority charge carriers is very small in reference to the doping concentration of the semiconductor substrate. Accordingly, high injection conditions are given if the product of maximum generation rate and effective life time range approximately about the doping concentration of the semiconductor substrate. Quasi steady-state measurements under low and high injection conditions are known per se and the respective measurement design and the parameters to generate these injection conditions are also known to one trained in the art.

In the above-mentioned preferred embodiment of the method according to the invention, as already described according to the processing steps A, B, and C, respectively the life time $\tau_{low}$ is determined at low injection conditions and the life time $\tau_{high}$ at high injection conditions.

In this preferred embodiment the temporal progression of the rate of generation is also determined quantitatively. Once more, a determination in relative units is sufficient for the temporal progression of the intensity of the photoluminescent radiation.

The effective life time $\tau$ of the semiconductor substrate in reference to the excess charge carrier density $\Delta n$ and/or the doping concentration N of the semiconductor substrate is determined in this preferred embodiment depending on the above-mentioned parameters. The determination occurs here preferably as follows: Due to the fact that the low-injection condition $\Delta n \ll N$ is fulfilled the equation 6 is reduced to a linear connection between a measurable luminescent signal and the excess charge carrier density:

$$\Phi_{low}(t) = A \cdot N \cdot \Delta n_{low}(t) \quad (10)$$

By the life time $\tau_{0,low}$ determined according to the above-described processing steps, when the maximum rate of generation $G_{0,low}$ (with the product of $\tau_{0,low}$ and $G_{0,low}$, being equivalent to the maximum excess charge carrier density) now the initially unknown factor $A \cdot N$ can be determined by measuring the intensity of the photoluminescent radiation $\Phi_{low}(t)$. With the ratio of the amplification factors of the luminescent signals between high and low injection measurements c the luminescent signal can be shown under high injection conditions analogous to the equation 6 as:

$$\Phi_{high}(t) = \frac{A}{c} \cdot \Delta n_{high}(t) \cdot (\Delta n_{high}(t) + N) = \frac{AN}{c} \cdot \Delta n_{high}(t) \cdot \left(\frac{\Delta n_{high}(t)}{N} + 1\right). \quad (11)$$

With the known AN/c and known $\tau_{0,high}$ and $G_{0,high}$ (and thus known maximum excess charge carrier density, see above) via a measurement of the intensity of the photoluminescent radiation $\Phi_{high}(t)$ of the equation 11 the doping concentration N can be determined. The determination of the injection-dependent life time can then be performed according to the above-described method using the continuity equation (equation 4).

Preferably the quantitative determination of the time-dependent progression of the rate of generation G(t) occurs as follows: By measuring the time-dependent photo flow of a photo-diode with a known spectral quantum efficiency at the sample location the current density of the excitation radiation $j_0$ can be measured. In a known spectrum (particularly for lasers: at known wavelength) the excitation radiation and known absorption coefficient of the semiconductor material $\alpha$ the rate of generation can also be determined as a function as the substrate depth z with the optic reflectivity of the sample surface R at the excitation wavelength:

$$G(z) = (1-R)j_0 \alpha \exp(-z\alpha) \quad (12)$$

Information regarding the entire substrate thickness provides the necessary value for the generation rate.

The present objection is further attained in a method for determining material parameters of a doped semiconductor substrate by measuring photoluminescent radiation according to claim 7. The method according to the invention as of claim 7 is based on a method of the self-consistent calibration, as described in T. Trupke, R. A. Bardos, M. D. Abbott, "Self-Consistent Calibration of Photoluminescence and Photoconductance Lifetime Measurements", Applied Physics Letters, 87: 184102, 2006.

The processing steps A through C are here equivalent to the processing steps described above.

It is essential that in the processing step C the effective life time of the minority charge carrier of the semiconductor substrate is determined depending on the excess charge carrier density $\tau(\Delta n)$ by which via a self-consistency method simultaneously a scaling parameter A and the doping concentration N of the semiconductor substrate are determined.

From the above-mentioned publication it is known that the time-dependent intensity of the photoluminescent radiation $\Phi(t)$ dependent upon the time dependent the excess charge carrier density $\Delta n(\tau)$, the doping concentration N, and a scaling factor A can be described. In the above-mentioned publication it is described that when known the doping concentration N the scaling parameter A can be determined as follows:

For an incorrect scaling factor A, when applying an excess charge carrier density is applied in reference to the effective life time a so-called hysteresis curve results. However, this is an artifact, which is based on the faulty conversion between the intensity of the photoluminescent radiation and excess charge carrier density due to the faulty calibration factor A. It is therefore possible by elimination of the rise of the hysteresis curve to determine the scaling factor A and this way from the measuring data the effective life time of the minority charge carrier, dependent on the excess charge carrier density.

Experiments of the applicant have shown that the minimizing of the hysteresis curve can be performed two-dimensionally with two undefined parameters, with one parameter being the above-mentioned scaling factor A and the other parameter the doping concentration N of the semiconductor substrate. Here, it is also possible to determine the effective life time depending on the excess charge carrier density without knowing or determining the doping concentration of the semiconductor substrate by another measuring method and furthermore the determination of the doping concentration N itself is also possible.

Preferably the minimizing occurs by defining an error function. Each access charge carrier density below the maximum achieved is given twice one is within the time progression of one excitation period (up/down). For each value pair of doping concentration N and calibration factor A according to the continuity equation (equation 4) here two life times $\tau_{up}$ and $\tau_{down}$ can be determined, which must be identical when the parameters N and A are selected correctly.

This error function includes the total of deviation squares of the differences occurring between the life times $\tau_{up}$ and $\tau_{down}$ developing at discrete, well-defined levels of the excess charge carrier density.

$$\chi(N, A) = \sum_i \left(2 \frac{\tau_{up}(\Delta n_i, N, A) - \tau_{down}(\Delta n_i, N, A)}{\tau_{up}(\Delta n_i, N, A) + \tau_{down}(\Delta n_i, N, A)}\right)^2 \quad (13)$$

The denominator in the equation 13 at the right side serves the purpose to prevent the calculation of particularly smaller square error totals in case of particularly small life times. This way the error function is without a unit. The global minimum of the error function $\chi(A,N)$ then discloses the desired parameters A and N by which then, at a given rate of generation G(t) using the equations 4 and 5, the life time can be determined as a function of the excess charge carrier density according to the above-described method.

It is also possible to expand this algorithm for minimizing a squared error total to several measurements, for example in case of different excitation intensities (low vs. high injection).

The development of a measuring device to perform the method according to the invention and the general procedure to perform the method according to the invention occurs in a manner known per se, similar to the QSS-PL-methods of prior art, as described for example in T. Trupke and R. A. Bardos, 31$^{st}$ IEEE PVSC, Orlando, 2005 and T. Trupke, R. A. Bardos, M. D. Abbott, "Self-Consistent Calibration of Photoluminescence and Photoconductance Lifetime Measurements", Applied Physics Letters, 87: 184102, 2005, with the assessment of the measurements here occurs deviating from the above-described way, though.

Preferably the time-resolved measurement of the intensity of the luminescent radiation Φ(t) occurs by a plurality of measurements successively measuring the intensity of the luminescent radiation. Preferably the measurement occurs with a clock rate ranging from 10-300 kHz, depending on the modulation period T (preferably at a range 10 Hz<$T^{-1}$<300 Hz), which depends on the expected life time.

The measurement of the temporal progression of the rate of generation G(t) preferably occurs such that the intensity of the excitation radiation is measured analogous to the intensity of the luminescent radiation, i.e. by a temporarily successive measuring of a plurality of measuring points for the intensity of the excitation radiation. The intensity of the excitation radiation measured is qualitatively equivalent to the temporal progression of the intensity of the generation rate. Here, preferably the measurement occurs with an identical clock frequency for measuring the luminescent radiation.

The determination of the quantitatively temporal progression of the rate of generation G(t) occurs preferably in the manner described above.

The modulation of the excitation radiation occurs periodically and preferably sinusoidal. In order to increase the precision of measurement preferably the measurement of the intensity of the excitation radiation and/or the intensity of the photoluminescent radiation occurs over a plurality of periods and subsequently an averaging of the measurements occurs. Beneficially the averaging occurs over measurement of at least 100, preferred at least 300, particularly preferred at least 500 periods in order to yield a sufficiently high signal-to-noise ratio after averaging the measurements.

The excitation radiation is preferably generated via a light source that can be modulated in a manner known per se. Particularly suitable are here lasers; however the use of LED-light sources is also within the scope of the invention.

The wavelength of the excitation radiation is preferably above the band edge of the semiconductor substrate and/or the spectrum of the excitation radiation to be measured and preferably ranges at least essentially above this band edge. The method according to the invention is particularly suitable for determining material parameters in silicon semiconductor substrates. Preferably the wavelength and/or the focus of the spectrum of the excitation radiation are therefore below 1000 nm, preferably below 900 nm. In particular the wavelengths range from 790 nm to 880 nm is suitable to perform the method according to the invention.

The method is preferably performed via a measurement design known per se from the QSS-PL—methods. Preferably the excitation radiation is guided, starting at a radiation source, such as a laser, via a beam splitter to the semiconductor substrate, with a portion of the excitation radiation being conducted via the beam splitter to the detection unit for measuring the temporal progression of the intensity of the excitation radiation. Here, particularly diodes are suitable for the detection unit. The beam splitter is preferably arranged and embodied such that only a small portion of the excitation radiation, beneficially less than 5%, preferably less than 2%, particularly less than 1% in reference to the intensity of the excitation radiation is conducted to the detection unit, so that the essential portion of the excitation radiation with regards to intensity impinges the semiconductor substrate to generate charge carrier pairs.

The intensity of the photoluminescent radiation is preferably measured via a diode in a method known per se. Here it is particularly advantageous to arrange the radiation source and the detection unit for the intensity of the photoluminescent radiation on oppositely located sides of the semiconductor substrate. This way the semiconductor substrate itself serves as a filter and shields the detection unit for the intensity of the photoluminescent radiation from the radiation source so that errors by the impingement of excitation radiation on the detection unit for the intensity of the photoluminscent radiation are avoided. Advantageously additional filters are arranged in the beam path between the semiconductor substrate and the detection unit for the intensity of the photoluminescent radiation to mask out the excitation radiation. Such filters are known per se in photoluminescent installations.

Additionally it is within the scope of the invention to arrange the radiation source and the detection unit for the intensity of the photoluminescent radiation on the same side of the semiconductor substrate. This way it is particularly possible to measure semiconductor structures, such as solar cells, which show on a rear side a partially or entirely covering metal coating, when using the method according to the invention. In this case it is mandatory to arranged filters to mask potentially reflected excitation radiation in the radiation path between the semiconductor substrate and the detection unit for the intensity of the photoluminescent radiation. This arrangement is known per se for measuring devices to measure photoluminescent radiation.

The measuring range of the semiconductor substrate, with its photoluminescent radiation being measured, is defined by the detection unit for the intensity of the photoluminescent radiation and/or potential optic elements (filters, lenses, blinds) in the radiation path between the semiconductor substrate and the detection unit. Preferably the measuring range only displays a section of the semiconductor substrate. Typically, the area of the measuring section projected to a surface of the semiconductor substrate ranges from 0.5 cm$^2$ to 12 cm$^2$, but it is variable beyond that.

In general, important information can already be gathered by the determination of the effective life time at one point of the semiconductor substrate with regards to the material quality of the semiconductor substrate. Additionally, the scope of the invention includes to perform a spatially resolved measurement of the material features of the semiconductor substrate at several spatial points via grid or scanning measuring methods, for example by a displacement of the semiconductor substrate on an XY-table.

Preferably the periodic modulation of the excitation radiation occurs such that the intensity of the excitation radiation shows precisely one maximum within a period.

BRIEF DESCRIPTION OF THE DRAWINGS

Additional preferred features and embodiments of the method according to the invention are described in the following based on the figures and an exemplary embodiment. Here, it shows.

DETAILED DESCRIPTION OF THE PREFERRED EMBODIMENTS

Figure 1:
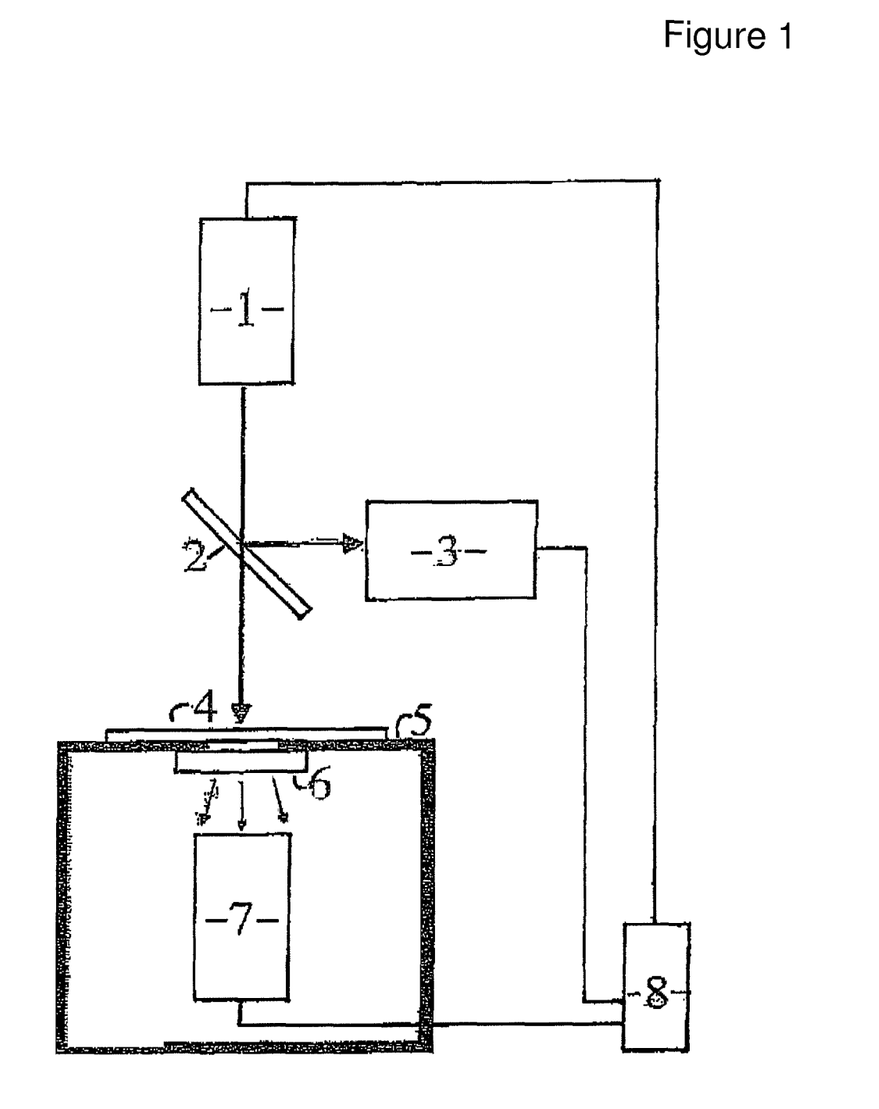
FIG. 1 a design to implement the method according to the invention.

The design shown in FIG. 1 comprises a light source 1, which is embodied as a laser diode with a wavelength of 880 nm. A beam splitter 2 is arranged in the radiation path of the excitation radiation, by which approximately 4% of the intensity of the excitation radiation is guided to a monitor diode 3, while the main portion of the excitation radiation impinges a semiconductor substrate 4 in a measuring area showing a size of approx. 4 cm$^2$. The semiconductor substrate 4 is a multicrystalline silicon wafer with a base doping of ~1 Ωcm.

The semiconductor substrate is arranged on a measuring table 5, at which an optic filter 6 and a PL-diode 7 are arranged in order to measure the intensity of the photoluminescent radiation emitted by the measuring area of the semiconductor substrate 4.

The filter 6 is here embodied such that radiation is masked in the wavelength range below 970 nm.

The radiation source 1, the monitor diode 3, and the PL-diode 7 are connected to a control and assessment unit 8 embodied as a computer.

In order to implement an exemplary embodiment of the method according to the invention the semiconductor substrate 4 is impinged with periodically modulated excitation radiation of the radiation source 1. Here, the modulation occurs sinusoidal. The intensity of the excitation radiation on the semiconductor substrate typically amounts to approx. $10^{16}$-$10^{19}$ cm$^{-2}$s$^{-1}$.

Using the monitor diode 3 the temporal progression of the intensity of the excitation radiation is measured qualitatively, with the measurement occurring with a clock rate of typically ~10-300 kHz.

Using the PL-diode 7 the temporal progression of the intensity of the photoluminescent radiation is measured qualitatively, with the measuring occurring with the same clock rate as in case of the excitation radiation.

The measuring series are recorded over 500 excitation periods and the respective individual measurements.

Figure 2:
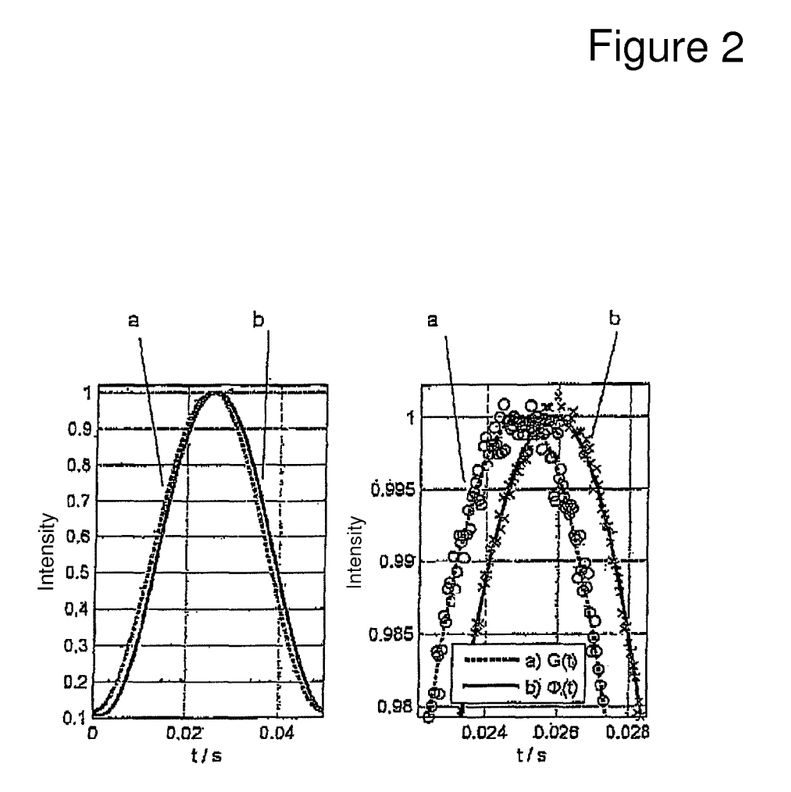
FIG. 2 measurements and fit-curves for the time-dependent generation rate G(t) and the intensity of the photoluminescent radiation Φ(t) and FIG. 3 the effective life time τ(Δn) determined from the measuring results.

The results of such a measurement are shown in FIG. 2.

Due to the fact that it represents qualitative measurements only the units normed to the value 1 are shown on the y-axis, the x-axis however shows quantitatively the temporal progression in seconds.

The measuring points allocated to the curve a are the measurements originating from the measurements of the monitor diode 3 and the measurement points allocated to the curve b (represent) the measuring data originating from the measurements of the PL-diode 7.

The continuous lines represent fit-curves to the respective measurement points, with the fit being based on a sinusoidal function of the amplitude 1 with the two undefined parameters of a time of maximum intensity to (respectively $t_{max}$) and a frequency.

$$f(t)=\cos^2(\omega(t-t_0)). \tag{14}$$

In FIG. 2 the temporal off-set of the maxima of the two curves is clearly discernible.

For an assessment the temporal displacements of the maxima of the generation rate G(t) (curve a) in reference to the maxima of the intensity of the luminescent radiation Φ(t) (curve b) are used for respectively slightly different intensities of excitation. For this purpose, the above-described iteration method is described using the numeric solution of the differential equation (equation 4) describing the dynamic of the charge carriers.

At an excessive charge carrier density of Δn=5.5·10$^{15}$ cm$^{-3}$ the determined life time amounts to τ=1.3·10$^{-3}$s.

Figure 3:
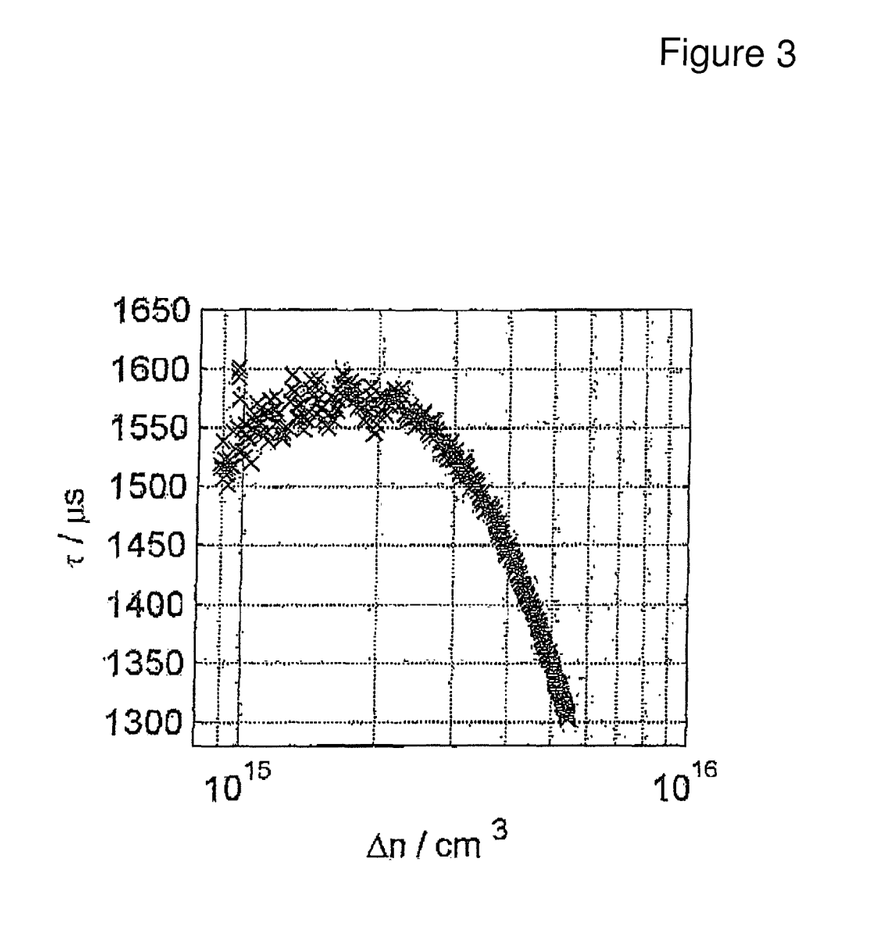

The doping concentrations, determined via the equation 9 from the ratio of the curvatures of the relative generation rate as well as the relative intensity of the photoluminescent radiation at its respective maxima amounts to N=1.2·10$^{15}$ cm$^{-3}$. Using the equation 4 here (as shown in FIG. 3) the life time can be determined as a function of the excessive charge carrier density.

Using the method according to the invention it is therefore possible for the first time, by assessing the photoluminescent radiation of a semiconductor substrate, to determine the effective life time at an arbitrary injection level without here it being necessary to know the doping concentration of the semiconductor substrate N. Additionally, N of the semiconductor substrate itself can be determined, here.

The invention claimed is:

1. A method for determining material parameters of a doped semiconductor substrate by measuring photoluminescent radiation comprising the following processing steps:
   A impinging the semiconductor substrate with an electromagnetic excitation radiation to generate luminescent radiation in the semiconductor substrate, with a temporal progression of an intensity of the excitation radiation being periodically modulated such that a generation rate G of charge carrier pairs, due to the excitation radiation, shows a maximum and a minimum during an excitation period in the semiconductor substrate (4), and with at least a relative temporal progression of the generation rate G(t) being determined via a time-dependent measurement of the intensity of the excitation radiation,
   B time-resolved measuring the intensity of the luminescent radiation emitted from a measuring area of the semiconductor substrate, with at least a relative temporal progression of an intensity of the luminescent radiation $\Phi(t)$ being measured at least during an excitation period,
   C determining at least one material parameter of the semiconductor substrate dependent on the temporal progression of the generation rate G(t) and the temporal progression of the intensity of the luminescent radiation $\Phi(t)$,
in step C an effective life time $\tau$ of the semiconductor substrate is determined at least for an excessive charge carrier density $\Delta n_{max}$ reached during one excitation period, by determining a temporal difference between a maximum of G(t) and a maximum of $\Phi(t)$ corresponding thereto.

2. A method according to claim 1, wherein in the processing step A an impingement with the excitation radiation occurs with different intensities:
   A impinging the semiconductor substrate at least twice with electromagnetic excitation radiation with respectively different maximum excitation intensities for generating luminescent radiation in the semiconductor substrate, with the temporal progression of the intensity of the excitation radiation being periodically modulated so that the generation rate G of charge carrier pairs shows a maximum and a minimum in the semiconductor substrate (4) during the excitation period due to the excitation radiation and with the temporal progression of the generation rate G(t) being determined via a time-dependent measurement of the intensity of the excitation radiation,
   B a time-resolved measuring of the respective intensities of the luminescent radiation emitted by the measuring area of the semiconductor substrate, with at least the relative temporal progressions of the intensities of the luminescent radiation $\Phi(t)$ being measured during one excitation period,
   C determining at least one material parameter of the semiconductor substrate dependent on the temporal progressions G(t) of the generation rate and the temporal progressions of the intensities of the luminescent radiation $\Phi(t)$,
with in step C the effective life time $\tau$ of the semiconductor substrate being determined at least in a range of the excessive charge carrier density $\Delta n_{max}$ maximally achieved during one excitation period by determining temporal differences between maxima of G(t) and respectively corresponding maxima of $\Phi(t)$.

3. A method according to claim 1, wherein in step C the effective life time $\tau(\Delta n)$ of the semiconductor substrate is determined dependent on excessive charge carrier density $\Delta n$ or doping concentration N of the semiconductor substrate, with the determination occurring dependent on the temporal progressions $\Phi(t)$ of the intensities of the photoluminescent radiation, measured at least in relative units, the quantitatively determined temporal progressions of the generation rate G(t), and the temporal differences between the maxima of G(t) and respectively corresponding maxima of $\Phi(t)$.

4. A method according to claim 3, wherein in step C the temporal progressions of the generation rate is described via a mathematic model, which has a first set of respectively at least two fit parameters, and the temporal progression of the intensities of the photoluminescent radiation is described via an analogous mathematic model, which shows a second set of at least two fit parameters each, and the fit parameters of the first set are determined dependent on the time-dependently measured intensities of the excitation radiation and the fit parameters of the second set dependent on the time-dependently measured intensities of the photoluminescent radiation, and the effective life time $\tau$ of the semiconductor substrate is determined depending on at least one of the excessive charge carrier density $\Delta n$ or the doping concentration N of the semiconductor substrate depending on the first and second set of fit parameters.

5. A method according to claim 4, wherein modulation of the excitation radiation is sinusoidal and the mathematical model for the temporal progressions of the generation rate and the temporal progressions of the intensities of the photoluminescent radiation each have a sinusoidal function and respectively a frequency and a phase position as the fit-parameters.

6. A method according to claim 5, wherein the excitation radiation is modulated such that an excessive charge carrier density of a minority charge carrier in the semiconductor substrate (4) at maximum generation is ideally approximately equivalent to an expected doping concentration of the semiconductor substrate.

7. A method according to claim 1, wherein the processing steps A and B are performed under at least two measuring configurations, different with regards to an excitation configuration, with a first measuring configuration being selected such that low-injection conditions are present in the semiconductor substrate (4) and a second measuring configuration is selected such that high-injection conditions are given, with in the first measuring configuration the life time, allocated to a maximum excessive charge carrier density, is determined from the temporal differences between the maxima of $G_{low}(f)$ and the respectively corresponding maxima of $\Phi_{low}(t)$ under low-injection conditions according to the iteration method of claim 1, as well as $G_{low}(t)$ being determined quantitatively, and accordingly in the second measuring configuration the life time allocated to the maximum excess charge carrier density, is determined from the temporal differences between the maxima of $G_{high}(t)$ and the respectively corresponding maxima of $\Phi_{high}(t)$ under high-injection conditions according to the iteration method of claim 1, as well as $G_{high}(t)$ is determined quantitatively and that, depending on the above-mentioned parameters, the effective life time $\tau(\Delta n)$ of the semiconductor substrate is determined depending on at least one of the excess charge carrier density $\Delta n$ or the doping concentration N of the semiconductor substrate.

8. A method for determining material parameters of a doped semiconductor substrate by measuring photoluminescent radiation comprising the following processing steps:

A impinging the semiconductor substrate with electromagnetic excitation radiation for generating luminescent radiation in the semiconductor substrate, with a temporal progression of an intensity of the excitation radiation being modulated periodically so that a generation rate G of charge carrier pairs in the semiconductor substrate (4), due to the excitation radiation during an excitation period, shows a maximum and a minimum, and with a temporal progression of the generation rate $G(t)$ being determined quantitatively via a time-dependent measurement of the intensity of the excitation radiation, B time-resolved measuring of an intensity of the luminescent radiation emitted by a measuring area of the semiconductor substrate, with at least a relative temporal progression of the intensity of the luminescent radiation $\Phi(t)$ being measured at least during the excitation period, C determining material parameters of the semiconductor substrate, depending on the temporal progression $G(t)$ of the generation rate and the temporal progression of the intensity of the luminescent radiation $\Phi(t)$ according to a self-consistent calibration method, the self-consistent calibration is performed with two calibration parameters, with one of the two parameters being a doping concentration N of the semiconductor substrate.

9. A method according to claim 8, wherein the determination of the two calibration parameters occurs via minimizing an error function in a two-dimensional parameter area.

10. A method according to claim 9, wherein for a self-consistent calibration measurements of the generation rate $G(t)$ and the intensity of the photoluminescent radiation $\Phi(t)$ are used for various injection conditions.

* * * * *